United States Patent [19]

Williams

[11] 4,167,335
[45] Sep. 11, 1979

[54] APPARATUS AND METHOD FOR LINEARIZING A VOLUME LOADING MEASUREMENT UTILIZING PARTICLE SCATTERING

[75] Inventor: Frederick L. Williams, Lansdale, Pa.

[73] Assignee: Leeds & Northrup Company, North Wales, Pa.

[21] Appl. No.: 861,224

[22] Filed: Dec. 16, 1977

[51] Int. Cl.² ............................................. G01N 15/02
[52] U.S. Cl. ................................... 356/336; 356/343
[58] Field of Search ............... 356/102, 103, 104, 336, 356/343

[56] References Cited

U.S. PATENT DOCUMENTS

| | | | |
|---|---|---|---|
| 3,310,680 | 3/1967 | Hasegawa | 356/104 |
| 3,358,148 | 12/1967 | Conklin et al. | 356/104 |
| 3,518,437 | 6/1970 | Riggs | 356/104 X |
| 3,873,206 | 3/1975 | Wilcock | 356/103 |

FOREIGN PATENT DOCUMENTS 722947  2/1955  United Kingdom ..................... 356/104

OTHER PUBLICATIONS

Monitor Technology, advertising brochure entitled, "The Monitor Approach, ".

*Primary Examiner*—John K. Corbin
*Assistant Examiner*—Matthew W. Koren
*Attorney, Agent, or Firm*—William G. Miller, Jr.; Raymond F. MacKay

[57] ABSTRACT

A method for linearizing the measurement of the volume loading of a fluid sample when it is determined by measuring the forward scattered light. The scattered light measurement which measures the volume loading is divided by a value related to a measure of the undiffracted light after it has passed through the sample.

8 Claims, 5 Drawing Figures

APPARATUS AND METHOD FOR LINEARIZING A VOLUME LOADING MEASUREMENT UTILIZING PARTICLE SCATTERING

BACKGROUND OF THE INVENTION

This invention relates to the use of forward diffracted light to measure the volume loading of a collection of particles suspended in a fluid sample. It is particularly applicable where, in the range being measured, the suspended particles are in such concentration that the forward diffracted light varies nonlinearly with changes in the volume loading. More particularly, this invention relates to the linearization of the relationship between the volume loading in the sample and the detected forward scattered light which is measured as a function of the volume loading. The volume loading is the total volume of the suspended particles per unit of sample. It has been found that as the total volume of the particles in a unit volume of sample increases beyond an initial low concentration the amount of scattered light detected does not vary in a substantially linear relationship with the changes in total particle volume. Instead the total particle volume varies in a nonlinear fashion with the change in the detected signal falling off as the concentration of particle volume increases.

It is an object of this invention to provide a method and means for linearizing the measurement of the volume loading as the volume loading of the sample varies over a wide dynamic range.

SUMMARY OF THE INVENTION

In carrying out the object of this invention, there is provided an improvement in the apparatus which is well known for measuring particles in fluid samples wherein that apparatus utilizes a light source for directing a coherent beam of light through a sample chamber to produce a signal in response to that portion of the forward diffracted light flux passed by a third power spatial filter such that the signal varies with changes in the volume loading. The improvement provides for linearizing the measurement and includes means for producing a signal responsive to the intensity of the undiffracted part of the light beam after it has passed through the sample chamber and means for dividing the signal representing the measurement of the volume loading by the signal representing the undiffracted light so as to produce a signal which is then a linear measure of volume loading.

DESCRIPTION OF THE PREFERRED EMBODIMENTS

Figure 1:
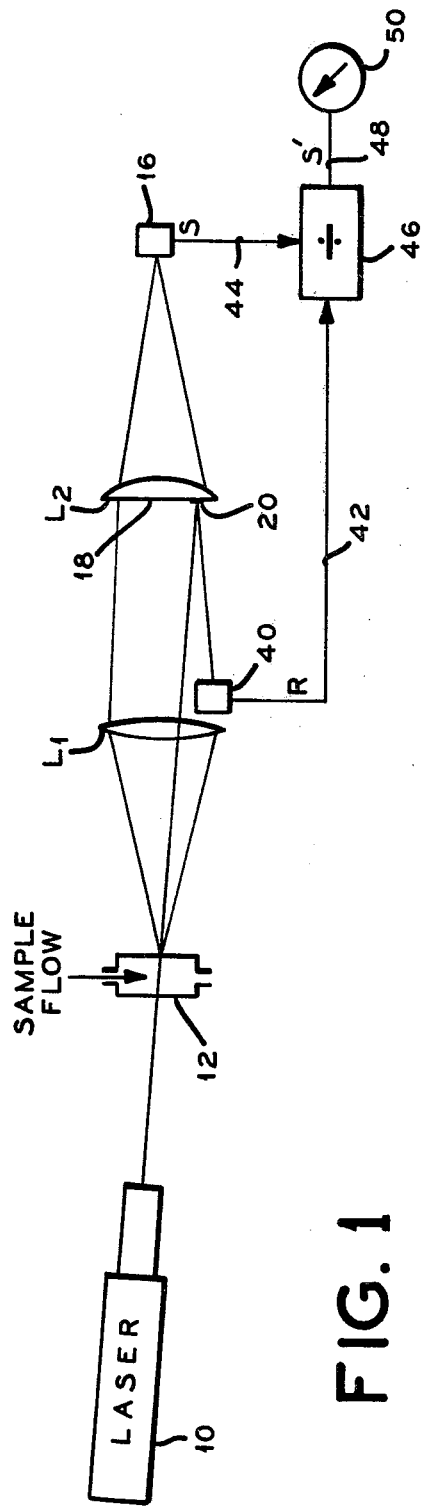
FIG. 1 is a diagram showing an embodiment of the invention.

In FIG. 1 there is shown a top view of a particle measuring system of the type shown and described in U.S. Pat. No. 3,873,206 which issued to William Leslie Wilcock on March 25, 1975 with the exception that the present particle measuring system includes a sample chamber for containing the sample within a small region.

Thus, in FIG. 1 the laser 10 functions to direct a coherent beam of light through the sample of fluid suspended particles contained in sample chamber 12. The low angle forward scattered light which is produced by the coherent beam striking the particles of the sample is collected by the lens $L_1$, and that diffracted light is transmitted through a spatial filter and focused by lens $L_2$ onto the photodetector 16 to provide a signal S indicating the intensity of the diffracted light transmitted by the filter and hence the magnitude of the volume loading of the particles in the collection in sample chamber 12.

The correlation between the light measured to produce the signal S and the volume loading depends upon the amount of diffracted light which is passed by the spatial mask 17, in the Fraunhofer plane of lens $L_1$ being reciprocally related to the first power of the radius from the center of the beam. The mask in FIG. 1 is formed on the surface of the plano-convex lens $L_2$. It will be noted that in FIG. 1 the light beam from the laser 10 is directed at an angle to the optical axis of the combination of lenses $L_1$ and $L_2$.

Figure 2:
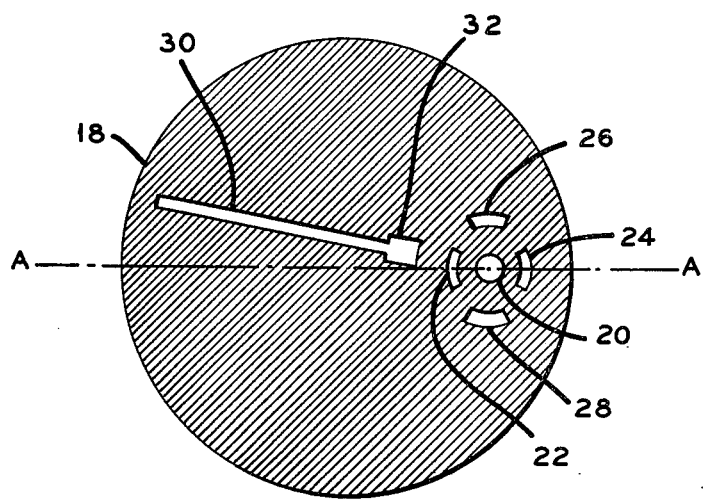
FIG. 2 is a layout drawing of one form of mask which can be used in the system of FIG. 1.

The mask 18 which may be formed on the surface of lens $L_2$ can, for example, have the form shown in FIG. 2.

The mask 18 has opaque regions shown as cross-hatched areas in FIG. 2 with the other regions of the mask being transparent with the exception of the spot 20 which defines a region which is reflective. Thus, in the mask 18 just outside the region of the spot 20, there are shown regions which are coaxial with the spot, namely regions 22 and 24, which are combined with the more distant regions 26 and 28 to provide the transparent areas for collecting the diffracted light information on the larger particles of the sample.

The information concerning the smaller particles of the sample is collected through the transparent region 30 which is in the form of a rectangular slit having an expanded region 32 at that end which is close to the spot 20. While the regions 20, 22, 24, 26, and 28 are symmetrically arranged about the horizontal axis A, the transparent regions 30 and 32 may be inclined at an angle to that axis as shown in FIG. 2. For example, the angle of inclination may be 10°. The purpose for so orienting the transparent regions 30 and 32 is to prevent interference from any incipient reflections.

Using an optical system as so far described, the magnitude of the signal S produced by the detector 16 will be related to the total volume per unit of sample or the volume loading of the particles suspended in the sample flowing through sample chamber 12 in accordance with the theory as discussed in the above mentioned Wilcock patent.

Figure 3:
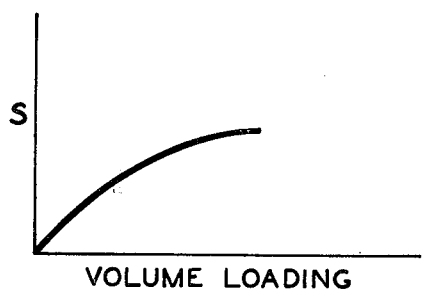
FIG. 3 is a graph showing the nonlinearity of the relationship between the volume loading of suspended particles over a wide range of volume loadings and the measured diffracted light.

It has been found that the volume loading measurement tends to be nonlinear with increased volume loadings as shown in FIG. 3. There is therefore no direct linear relationship between the signal S and the volume per unit sample of the particles in the sample.

In order to establish a linear relationship between the signal S and the volume loading so that a linear relationship is maintained in the final measured value over a wide range of values, there is provided, as shown in FIG. 1, a means for detecting the intensity of the undiffracted part of the light beam after it has passed through the sample chamber. Thus, there is reflected from the spot 20 of the mask on the surface 18 of the lens $L_2$ the undiffracted beam of light after it has passed through the sample chamber 12 as well as the lens $L_1$. That beam is reflected to impinge upon the photodetector 40 which responds to provide on its output line 42 a signal R representative of the intensity of the undiffracted light beam.

The signal on line 42 is then divided into the signal S provided on line 44 by the divider 46 so as to produce on the output line 48 of that divider a signal which may be utilized as an input to the indicator 50 so as to provide an indication of the volume of the particles per unit sample. That resulting indication will be linear over a wide range of measurements.

The calculation carried out by the divider 46 and the resulting indication provided by the indicator 50 may be construed from a theoretical point of view by considering that the normal volume response of the detector 16 and hence the value of the signal S may be expressed as follows:

$$S = Ik \int_0^\infty a^3 D_n(a) da$$

where I is the effective illumination of the particles, k is an instrument constant and the integral is the desired volumetric scattering function provided by the spatial filter where "a" represents the diameter of the particles.

The nonlinearity in S with respect to changes in volumetric loading, as shown in FIG. 3, is due to the fact that the laser beam is attenuated by the particles which are illuminated by the laser and which scatter a certain portion of the laser intensity out of the central beam. Thus it is necessary to compensate for these variations in the attenuation caused by the particles in the sample. This compensation is also effective to compensate for changes in the intensity of the laser output itself.

Thus, we may consider that $I=I_oT$ where $I_o$ is the incident light intensity and $T=1-A$ where A is the light beam attenuation within the sample chamber. Thus, the desired measurement is $S'=S/I_oT$. It will be evident from FIG. 1 that the signal output from the photodetector 40, namely R, is equal to $I_oT$ and therefore the division carried out by divider 46 provides the signal S on line 48 to indicator 50.

Applicant has used the term particle in a broad sense in this description in that it is used to indicate solids suspended in fluids which may be either liquid or gas and also to represent bubbles in liquids which are known to those familiar with the art to provide forward diffracted light patterns similar to those provided by suspended solids.

The arrangement of FIG. 1 has been found to be very useful in making volume loading measurements of suspended solids in applications such as sewage treatment as well as other applications where the amount of suspended solids tends to be great thus causing the measurement to be carried out in that region of FIG. 3 which is nonlinear.

Figure 4:
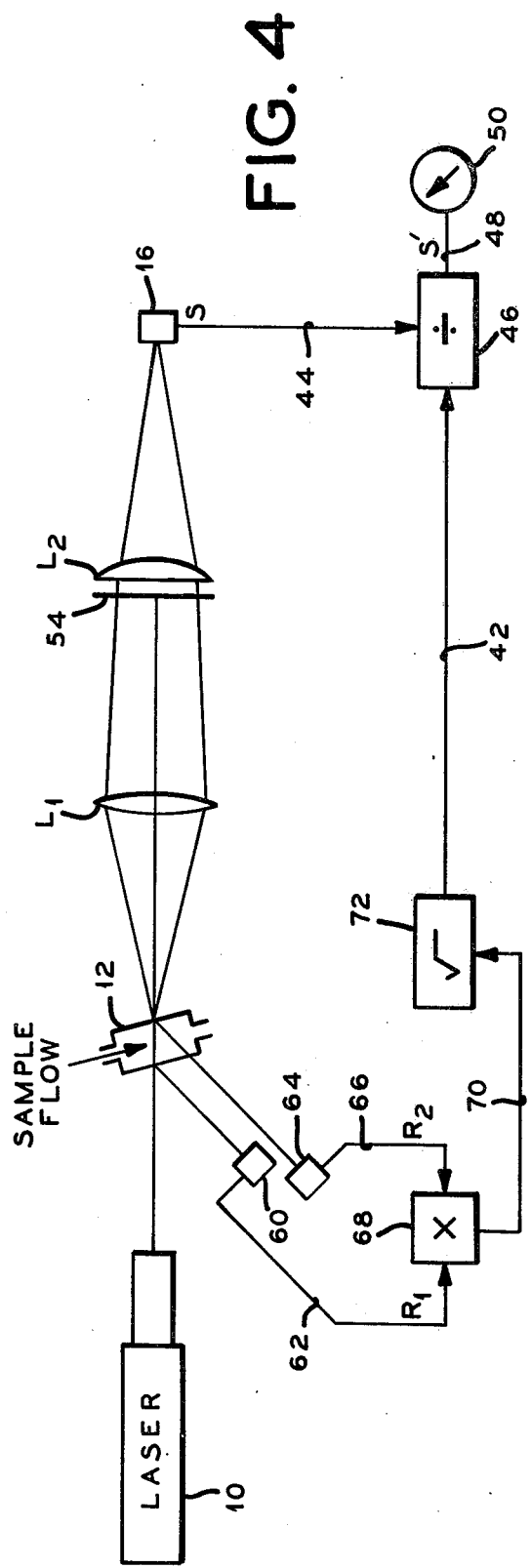
FIG. 4 is a diagram of another embodiment of the invention.

Still another system for obtaining a similar linearization of the measurement of a dimensional characteristic of fluid suspended particles is shown in FIG. 4. FIG. 4 utilizes an optical system similar to that of FIG. 1 in that the laser 10 directs a coherent beam of light through the sample chamber 12 so that the forward diffracted light from the particles in the sample is collected by the lens $L_1$ and directed through the separate mask 54 and then through the lens $L_2$ which focuses the light passed by the mask 54 on the detector 16 so that it can provide a signal S on its output line 44 which can be divided by the signal on line 42 by the divider 46 so as to produce on line 48 an output signal to the indicator 50 which is similar to that shown in the arrangement in FIG. 1.

FIG. 4 differs from FIG. 1, however, in that in FIG. 4 the sample chamber 12 is necessarily made up of parallel opposing flat sides positioned at an angle to the optical axis which in FIG. 4 is the same for both the laser beam and the optical system made up of the lenses $L_1$ and $L_2$. With the sample chamber 12 so oriented, there is a reflection from the exterior surface of the sample chamber where the light beam from the laser 10 strikes the surface of the sample chamber at the point where the beam enters the sample chamber. That reflection of the light beam is directed to the photodetector 60 which responds by producing a signal $R_1$ on line 62.

The undiffracted portion of the light beam, after it has passed through the sample, is reflected from the interior surface of the wall of the sample chamber 12 where the beam exits the chamber. That reflection is directed to the photodetector 64 which produces a signal $R_2$ on its output line 66.

The signals on lines 62 and 66 are multiplied by the multiplier 68 to produce an output signal on line 70 into the square root extractor 72. Thus, the signal on line 70 represents $R_1 \times R_2$ and the output of the square root extractor 72 on line 42 represents the square root of that quantity.

It will be evident that the signal on line 42 in FIG. 4 is similar to that on line 42 of FIG. 1 when one considers that the signal $R_1$ is proportional to $I_o$ and the signal $R_2$ is proportional to $I_oT^2$. Thus, $$R_1 \times R_2 = k_o(I_oT)^2$$

and $I_oT$ can be obtained by a square root operation.

Figure 5:
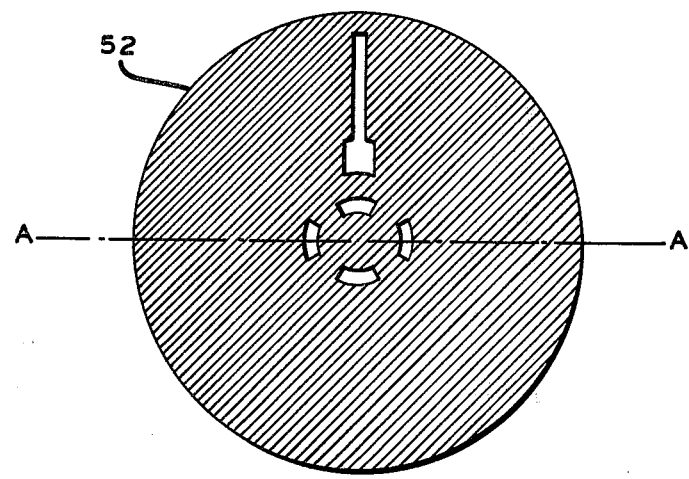
FIG. 5 is a layout drawing showing one form for the mask of FIG. 4.

The mask 54 in FIG. 4 may have a configuration such as that shown in FIG. 5 wherein the opaque regions of the mask are shown as crosshatched areas with the other regions being transparent and having a configuration similar to that of FIG. 2 except that the various transparent areas are oriented symmetrically about the center of the mask rather than about a reflecting spot 20 near the edge of the mask forming the filter as in FIG. 2. The mask of FIG. 5 contains no reflective spots but is otherwise similar to the mask of FIG. 2 except for the orientation of the axis about which the transparent areas are arranged.

In producing the mask 18 to cover the plane surface of lens $L_2$, it has been found useful to deposit chromium on the lens surface in the regions to be made opaque as well as in the region where the reflective spot 20 is located. Those regions which are to remain opaque are then oxidized so as to be nonreflective with the spot 20 being nonoxidized. By following this method of manufacture, it is possible to conveniently orient the spot 20 with respect to the transparent parts of the mask without great difficulty.

What is claimed is:

1. In apparatus for measuring the volume loading of a collection of suspended particles in a fluid sample when the volume loading is sufficient to cause the intensity of the forward scattered light passed by a third power spatial filter to vary nonlinearly with changes in the volume loading, wherein the apparatus utilizes a light source for directing a coherent beam of light through a sample chamber and produces a first signal in response to the forward diffracted light flux passed by said filter so that said first signal varies with the change in volume loading;

the improvement comprising:

means for producing a second signal responsive to the intensity of the undiffracted part of said light beam after it has passed through said sample; and means for dividing said first signal by said second signal to thereby produce a linear measurement of said volume loading.

2. Apparatus according to claim 1 in which said means for producing said second signal includes a single photocell to measure the intensity of the undiffracted beam after it has passed through said sample.

3. In apparatus for measuring the volume loading of a collection of suspended particles in a fluid sample when the volume loading is sufficient to cause the intensity of the forward scattered light passed by a third power spatial filter to vary nonlinearly with changes in the volume loading, wherein the apparatus utilizes a light source for directing a coherent beam of light through a sample chamber and produces a first signal in response to the forward diffracted light flux passed by said filter so that said first signal varies with the change in volume loading;

the improvement comprising:

means for producing a second signal responsive to the intensity of the undiffracted part of said light beam after it has passed through said sample, said means including a first photocell to measure the light reflected from the exterior surface of the sample where the beam strikes the surface of the chamber as the beam enters the sample chamber, a second photocell to measure the undiffracted light reflected from the interior surface of the wall of the sample chamber where the beam exits the chamber after it has passed back through said sample, and means for extracting the square root of the product of the outputs of the said first and second photocells to produce said second signal; and means for dividing said first signal by said second signal to thereby produce a linear measurement of said volume loading.

4. Apparatus according to claim 1 in which said means for producing said second signal includes:

a photocell; and a reflective spot in the path of said undiffracted part of said beam positioned to reflect said undiffracted beam on said photocell to provide from said photocell said second signal.

5. An improved apparatus for measuring the volume loading of a collection of particles suspended in a fluid sample, which apparatus measures a portion of the light diffracted by said particles from a coherent light beam directed through said sample to produce a signal whose magnitude varies with the volume of said particles, the improvement comprising:

means responsive to the intensity of the undiffracted portion of said beam after it has passed through said sample for producing another signal representing the intensity of said undiffracted beam; and means for dividing said diffracted light signal by said other signal to produce a resulting signal having a linear relationship to the magnitude of said volume loading over a wide range of values.

6. The method for linearizing a signal representing the measurement of the volume loading of a collection of particles suspended in a fluid sample when the volume loading of the particles is sufficient to cause the measured portion of the forward diffracted light produced by a coherent beam directed on the sample to vary nonlinearly with changes in said volume loading comprising the steps of:

producing a signal in response to the intensity of the undiffracted part of said light beam after it has passed through the sample; and dividing said last named signal into said first named signal to produce said linearized measurement.

7. Apparatus for measuring the volume loading of a collection of suspended solids in a flowing fluid sample comprising:

a sample chamber through which said sample flows;

a source producing a coherent light beam directed through said sample chamber;

a first and second photodetector;

a first lens for collecting the forward diffracted light from said sample on one side of said beam;

a spatial filter in the Fraunhofer plane of said first lens, said filter having a transmission factor which varies as a function of the distance from the axis of said beam so that the total light flux transmitted due to said solids is a function of the total volume of said solids per unit volume of said sample;

a second lens for focusing the diffracted light passed by said filter on said first photodetector to produce a first signal responsive to the diffracted light from said sample;

a reflective spot positioned to reflect onto said second photodetector the undiffracted portion of said beam after it has passed through said sample to produce a second signal responsive to said undiffracted beam; and means for dividing said first signal by said second signal to thereby produce a resulting signal which has a linear relationship to the volume loading of the sample over a range of loadings including regions in which the first signal has a nonlinear response to changes in volume loading.

8. Apparatus for measuring the volume loading of a collection of suspended solids in a flowing fluid sample comprising:

a sample chamber through which said sample flows, said sample chamber having parallel opposing flat sides;

a source producing a coherent light beam directed through said sample chamber at an angle to said flat sides;

a first photodetector;

a first lens for collecting the forward diffracted light from said sample;

a spatial filter in the Fraunhofer plant of said first lens, said filter having a transmission factor which varies as a function of the distance from the axis of said beam so that the total light flux transmitted due to said solids is a function of the total volume of said solids per unit volume of said sample;

a second lens for focusing the diffracted light passed by said filter on said first photodetector to produce a first signal S responsive to the diffracted light from said sample;

a second detector positioned to receive the reflection of the incident beam from the exterior side of said sample chamber where said beam enters said sample to produce a second signal $R_1$;

a third photodetector positioned to receive the reflection of the light beam from the interior surface of that side of the sample chamber from which said beam exits after it has passed through said sample subsequent to its reflection to produce a third signal $R_2$; and means for producing a resulting signal by calculating the quantity $S/\sqrt{R_1 \times R_2}$ which has a linear relationship to the volume loading of the sample over a range of loadings including regions in which the first signal has a nonlinear response to changes in volume loading.

* * * * *